United States Patent
Tsui

(10) Patent No.: US 12,410,461 B2
(45) Date of Patent: *Sep. 9, 2025

(54) METHOD OF PREPARING CLINICAL SAMPLES FOR NUCLEIC ACID AMPLIFICATION

(71) Applicant: Day Zero Diagnostics, Inc., Boston, MA (US)

(72) Inventor: Chiahao Tsui, Somerville, MA (US)

(73) Assignee: Day Zero Diagnostics, Inc., Watertown, MA (US)

( * ) Notice: Subject to any disclaimer, the term of this patent is extended or adjusted under 35 U.S.C. 154(b) by 1046 days.

This patent is subject to a terminal disclaimer.

(21) Appl. No.: 17/434,293

(22) PCT Filed: Feb. 28, 2020

(86) PCT No.: PCT/US2020/020275
§ 371 (c)(1),
(2) Date: Aug. 26, 2021

(87) PCT Pub. No.: WO2020/176822
PCT Pub. Date: Sep. 3, 2020

(65) Prior Publication Data
US 2022/0127660 A1    Apr. 28, 2022

Related U.S. Application Data

(63) Continuation of application No. 16/289,324, filed on Feb. 28, 2019, now Pat. No. 10,544,446.

(60) Provisional application No. 62/812,085, filed on Feb. 28, 2019.

(51) Int. Cl.
*C12Q 1/6806*    (2018.01)
*C12Q 1/6848*    (2018.01)

(52) U.S. Cl.
CPC ......... *C12Q 1/6806* (2013.01); *C12Q 1/6848* (2013.01)

(58) Field of Classification Search
None
See application file for complete search history.

(56) References Cited

U.S. PATENT DOCUMENTS

| | | | |
|---|---|---|---|
| 9,719,128 | B2 | 8/2017 | Fuchs et al. |
| 10,544,446 | B1 | 1/2020 | Tsui |
| 2006/0018797 | A1 | 1/2006 | Burnell et al. |
| 2006/0019258 | A1 | 1/2006 | Yeakley |
| 2009/0161497 | A1 | 6/2009 | Collis et al. |
| 2018/0142231 | A1 | 5/2018 | Kubicek et al. |

FOREIGN PATENT DOCUMENTS

| CN | 102471768 A | 5/2012 |
|---|---|---|
| EP | 1201753 A1 | 5/2002 |
| JP | 2008-067718 A | 3/2008 |
| WO | WO 2016/024263 A1 | 2/2016 |
| WO | WO 2017/042819 A1 | 3/2017 |

OTHER PUBLICATIONS

Extended European Search Report mailed Oct. 31, 2022 for Application No. EP 20762414.9.
Holodniy et al., Inhibition of human immunodeficiency virus gene amplification by heparin. J Clin Microbiol. Apr. 1991;29(4):676-9. doi: 10.1128/jcm.29.4.676-679.1991.
International Search Report and Written Opinion for Application No. PCT/US2020/020275 mailed Jun. 10, 2020.
International Preliminary Report on Patentability for Application No. PCT/US2020/020275 mailed Sep. 10, 2021.
Belding et al., Effect of sodium polyanetholsulfonate on antimicrobial systems in blood. Appl Microbiol. Nov. 1972;24(5):691-8.
Boedicker et al., Detecting bacteria and determining their susceptibility to antibiotics by stochastic confinement in nanoliter droplets using plug-based microfluidics. Lab Chip. Aug. 2008;8(8): 1265-72. doi: 10.1039/b80491 1d. Epub Jul. 4, 2008. Author manuscript.
Boehm et al., On-chip microfluidic biosensor for bacterial detection and identification. Sensors and Actuators B: Chemical. Oct. 1, 2007:126(2):508-514.
Cady et al., Real-time PCR detection of Listeria monocytogenes using an integrated microfluidics platform. Sensors and Actuators B: Chemical. May 27, 2005:107(1):332-341.
Cho et al., One-step pathogen specific DNA extraction from whole blood on a centrifugal microfluidic device. Lab Chip. May 2007;7(5):565-73. Epub Feb. 15, 2007.
Edberg et al., Use of sodium polyanethol sulfonate to selectively inhibit aminoglycoside and polymyxin antibiotics in a rapid blood level antibiotic assay. Antimicrob Agents Chemother. Mar. 1976;9(3):414-7.
Fredricks et al., Improved amplification of microbial DNA from blood cultures by removal of the PCR inhibitor sodium polyanetholesulfonate. J Clin Microbiol. Oct. 1998;36(10):2810-6.
Hou et al., Direct detection and drug-resistance profiling of bacteremias using inertial microfluidics. Lab Chip. May 21, 2015;15(10):2297-307. doi: 10.1039/c51c003llc. Author manuscript.
Khaledi et al., Transcriptome Profiling of Antimicrobial Resistance in Pseudomonas aeruginosa. Antimicrob Agents Chemother. Jul. 22, 2016;60(8):4722-33. doi: 10.1128/AAC.00075-16. Print Aug. 2016.
Kiehl et al., Anticoagulants as inhibitors of reverse transcriptase activity. J Natl Cancer Inst. Nov. 1973;51(5):1705-7.
Kocka et al., Action of sulfated polyanions used in blood culture on lysozyme, complement and antibiotics. Ann Clin Lab Sci. Nov.-Dec. 1972;2(6):470-3.
Lee et al., Synthetic ligand-coated magnetic nanoparticles for microfluidic bacterial separation from blood. Nano Lett. Jan. 8, 2014;14(1):1-5. doi: 10.1021/nl3047305. Epub Jan. 31, 2013.

(Continued)

*Primary Examiner* — Samuel C Woolwine
(74) *Attorney, Agent, or Firm* — Wolf, Greenfield & Sacks, P.C.

(57) ABSTRACT

The present disclosure is a method of preparing a clinical sample comprising host cells, microbes, proteins and a polyanionic polymer nucleic acid amplification inhibitor.

19 Claims, 7 Drawing Sheets

(56) References Cited

OTHER PUBLICATIONS

Mahalanabis et al., Cell lysis and DNA extraction of gram-positive and gram-negative bacteria from whole blood in a disposable microfluidic chip. Lab Chip. Oct. 7, 2009;9(19):2811-7. doi: 10.1039/b905065p. Epub Jun. 29, 2009.

Pennington, Dealing with amplification inhibitors: reagent choice matters. Promega Corporation. Feb. 2014. Retrieved from the Internet: <https://www.promega.com/-/media/files/promega -worldwide/north-america/promega -us/webinars-and-events/2014/dealingwith-amplification-inhibitors-webinar-Feb. 2014.pdf?la=en> on Mar. 13, 2019. 57 pages.

Qian et al., Direct identification of bacteria from positive blood cultures by amplification and sequencing of the 16S rRNA gene: evaluation of BACTEC 9240 instrument true-positive and false-positive results. J Clin Microbial. Oct. 2001;39(10):3578-82.

Regan et al., A sample extraction method for faster, more sensitive PCR-based detection of pathogens in blood culture. J Mol Diagn. Mar.-Apr. 2012. 14(2):120-9. doi: 10.1016/j.jmoldx.2011.10.001. Epub Jan. 11, 2012.

Traub et al., Inactivation of classical and alternative pathway-activated bactericidal activity of human serum by sodium polyanetholsulfonate. J Clin Micro biol. Mar. 1977;5(3):278-84.

Xia et al., Combined microfluidic-micromagnetic separation of living cells in continuous flow. Biomed Microdevices. Dec. 2006;8(4):299-308.

Yung et al., Micromagnetic-microfluidic blood cleansing device. Lab Chip. May 7, 2009;9(9):1171-7. doi: 10.1039/b816986a. Epub Feb. 18, 2009.

METHOD OF PREPARING CLINICAL SAMPLES FOR NUCLEIC ACID AMPLIFICATION

RELATED APPLICATIONS

This application is a national stage filing under 35 U.S.C. § 371 of international application number PCT/US2020/020275, filed Feb. 28, 2020 and published under PCT Article 21 (2) in English, which is a continuation of U.S. application Ser. No. 16/289,324, filed Feb. 28, 2019 and issued as U.S. Pat. No. 10,544,446, and which claims the benefit under 35 U.S.C. § 119 (e) of U.S. provisional application Ser. No. 62/812,085, filed Feb. 28, 2019, each of which is herein incorporated by reference in its entirety.

FIELD OF THE INVENTION

The invention relates generally to the field of clinical sample preparation, and specifically to reducing the negative effects on nucleic acid amplification detection caused by certain additives to clinical samples.

BACKGROUND

Hospital-acquired pathogenic microbial infections require rapid identification of the microbe(s) present to ensure appropriate antimicrobial treatment. On any given day, about 1 in 31 hospital patients has at least one hospital-acquired pathogenic microbial infection. In 2015, there were an estimated 687,000 hospital-acquired pathogenic microbial infections, resulting in 72,000 deaths. Administration of the broad-spectrum, non-targeted antimicrobials to patients with these hospital-acquired microbial infections can lead to antimicrobial resistance.

The preservation of microbes in clinical samples obtained from subjects with pathogenic microbial infections is critical for subsequent clinical diagnostic tests. To that end, polyanionic detergents are effective for inhibiting bactericidal processes in whole blood, such as the complement pathway, and are commonly used in blood culture bottles to promote the survival and growth of bacteria in samples (Edberg et al., 1976, "Use of sodium polyanethol sulfonate to selectively inhibit aminoglycoside and polymyxin antibiotics in a rapid blood level antibiotic assay," Antimicro. Agents Chemother. 9(3): 414-417; Kocka et al., 1972, "Action of sulfated polyanions used in blood culture on lysozyme, complement, and antibiotics," Ann. Clinc. Lab. Sci. 2(6): 470-473; Traub and Kleber, 1977, "Inactivation of classical and alternative pathway-activated bactericidal activity of human serum by sodium polyanethol sulfonate," J. Clin. Microbiol. 5(3): 278-284).

Next-generation molecular diagnostics (e.g., nucleic acid amplification) for the identification of bacteria from clinical blood samples offers a rapid alternative to the traditional cultivation of bacteria. However, polyanionic compounds which are commonly added to clinical samples, such as sodium polyanethol sulfonate (SPS) to inhibit bactericidal processes and heparin to inhibit clotting, have an inhibitory effect on nucleic acid amplification techniques (Fredericks and Relman, 1998, "Improved amplification of microbial DNA from blood cultures by removal of the PCR inhibitor sodium polyanethol sulfonate," J. Clin. Microbiol., 36(10): 2810-2816; Qian et al., 2001, "Direct identification of bacteria from positive blood cultures by amplification and sequencing of the 16S rRNA gene: evaluation of BACTEC 9240 instrument true-positive and false-positive results," J. Clin. Microbiol., 39 (10: 3578-3585; and Regan et al., 2012, "A sample extraction method for faster, more sensitive PCR-based detection of pathogens in blood culture," J. Mol. Diagn. 14(2): 120-129). In addition to such additives, blood components such as hemoglobin, lactoferrin, heme, and immunoglobulins can also interfere with nucleic acid amplification procedures. Chemical similarities between nucleic acids and polyanionic polymers such as SPS, however, lead to the co-purification of both polymers in multiple nucleic acid purification techniques, thereby resulting in inhibition of downstream molecular applications (Regan et al., 2012, supra).

Improved methods are needed to reduce the negative effects of certain common additives and naturally-occurring compounds (e.g., SPS, heparin) on nucleic acid amplification-based diagnostics during the processing of clinical samples. Current methods of clinical sample processing for downstream nucleic acid amplification currently dilute final samples from 10× to 1000× to mitigate SPS inhibition. However, these approaches also significantly reduce nucleic acid detection sensitivity (Pennington, 2014, "Dealing with amplification inhibitors: reagent choice matters," Promega Corporation).

SUMMARY

The present invention depends, in part, upon the discovery that adding proteases to clinical samples reduces contamination by certain nucleic acid amplification inhibitors in processed clinical samples, without otherwise substantially harming the integrity or quality of the samples, and thereby improves nucleic acid amplification of the same. Improved nucleic acid amplification also allows for improved detection of rare nucleic acids in mixed samples, such as microbial DNA in human patient-derived clinical samples.

Thus, in one aspect, the present disclosure provides methods for preparing a clinical sample from a subject comprising cells from the subject, microbes, and a polyanionic polymer nucleic acid amplification inhibitor that binds to at least one protein in the sample. In some embodiments, the method comprises: (a) obtaining the clinical sample from the subject comprising cells from the subject, the microbes, the plasma protein, and the polyanionic polymer nucleic acid amplification inhibitor, (b) separating the clinical sample into a first fraction comprising the cells of the subject and a second fraction comprising the microbes and the polyanionic polymer nucleic acid amplification inhibitor bound to the protein, (c) adding to the second fraction a protease which degrades the protein, and (d) separating the second fraction into a third fraction comprising the microbes and a fourth fraction comprising the polyanionic polymer nucleic acid amplification inhibitor.

In another aspect, the present disclosure provides methods for preparing a clinical sample from a subject comprising microbes, and a polyanionic polymer nucleic acid amplification inhibitor that binds at least one protein in the sample, comprising the steps of: (a) obtaining the clinical sample from the subject comprising the microbes and the polyanionic polymer nucleic acid amplification inhibitor, (b) adding to the sample a protease which degrades the protein, (c) separating the clinical sample into a first fraction comprising the cells of the subject and a second fraction comprising the microbes and the polyanionic polymer nucleic acid amplification inhibitor bound to the protein, (d) removing the second fraction from the first fraction, and (e) separating the second fraction into a third fraction comprising the microbes and a fourth fraction comprising the polyanionic polymer nucleic acid amplification inhibitor.

In another aspect, the present disclosure provides a method for preparing a clinical sample from a subject comprising microbes, cells, and at least one polyanionic polymer nucleic acid amplification inhibitor that binds at least one protein in the sample, comprising the steps of: (a) obtaining the clinical sample from the subject comprising the microbes, the protein and the polyanionic polymer nucleic acid amplification inhibitor, (b) adding to the clinical sample a protease which degrades the protein, (c) separating the clinical sample into a first fraction comprising the cells of the subject and a second fraction comprising the microbes and the polyanionic polymer nucleic acid amplification inhibitor bound to the protein, (d) removing the second fraction from the first fraction, (e) separating the second fraction into: a third fraction comprising the microbes and a fourth fraction comprising the polyanionic polymer nucleic acid amplification inhibitor.

In another aspect, the present disclosure provides a method for preparing a clinical sample from a subject comprising microbes, cells, and at least one polyanionic polymer nucleic acid amplification inhibitor that binds at least one protein in the sample, comprising the steps of: (a) obtaining the clinical sample from the subject comprising the microbes, the protein, and the polyanionic polymer nucleic acid amplification inhibitor, (b) separating the clinical sample into: a first fraction comprising the cells of the subject and a second fraction comprising the microbes and the polyanionic polymer nucleic acid amplification inhibitor bound to the protein (c) removing the second fraction from the first fraction, (d) adding to the second fraction a protease which degrades the protein in the second fraction after step (b) or step (c), (e) separating the second fraction into a third fraction comprising the microbes and a fourth fraction comprising the polyanionic polymer nucleic acid amplification inhibitor.

In another aspect, the present disclosure provides a method for preparing a clinical sample from a subject comprising microbes, and at least one polyanionic polymer nucleic acid amplification inhibitor that binds at least one protein in the sample, comprising the steps of: (a) obtaining the clinical sample from the subject comprising the microbes, the protein, and the polyanionic polymer nucleic acid amplification inhibitor, (b) selectively lysing the microbes, (c) adding to the clinical sample a protease which degrades the protein, (d) separating the clinical sample into a first fraction comprising the cells of the clinical sample and a second fraction comprising nucleic acid from the microbes.

In some embodiments of each of the foregoing aspects, the methods further comprise the step of amplifying the microbial nucleic acid.

In some embodiments of each of the foregoing aspects, the separating is by centrifugation. In some embodiments of each of the foregoing aspects, the separating is by microfluidics. In some embodiments of each of the foregoing aspects, the separating is by immunoprecipitation. In some embodiments of each of the foregoing aspects, the separating is by filtration.

In some embodiments of each of the foregoing aspects, the obtaining step utilizes a vacuum liquid container. In some embodiments of each of the foregoing aspects, the obtaining step utilizes a blood culture bottle. In some embodiments of each of the foregoing aspects, the obtaining step is receiving a sample from a health care provider.

In some embodiments of each of the foregoing aspects, the protease is selected from the group consisting of: proteinase K, Factor Xa, Arg-C proteinase, Asp-N endopeptidase, Asp-N endopeptidase+N-terminal Glu, 3-Bromo-3-methyl-2-(2-nitropheylthio-)-3H-indole (BNPS-Skatole), Caspase1, Chymotrypsin-high specificity, Clostripain, cyanogen bromide (CNBr), Enterokinase, Granzyme B, formic acid, glutamyl endopeptidase, hydroxylamine, iodosobenzoic acid, LysC, LysN, 2-nitro-5-thiocyanatobenzoic acid (NCTB), pepsin, proline-endopeptidase, staphylococcal peptidase I, tobacco etch virus protease, thermolysin, thrombin, and trypsin. In some embodiments of each of the foregoing aspects, the amount of protease added is between 5 units (U) and 5000 U. In some embodiments of each of the foregoing aspects, the protease and supernatant are incubated at between 20° C. and 55° C. for between 10 minutes and 120 minutes.

In some embodiments of each of the foregoing aspects, the nucleic acid amplification is isothermal strand-displacement amplification, PCR, qPCR, RT-PCR, degenerate oligonucleotide PCR, or primer extension pre-amplification.

In some embodiments of each of the foregoing aspects, the nucleic acid amplification is by phi29 DNA polymerase, Bst DNA polymerase Large Fragment, or DNA Polymerase I Klenow Fragment.

In some embodiments of each of the foregoing aspects, the addition of protease increases the amplification of microbial nucleic acid by between 5-fold and 100-fold.

In some embodiments, of each of the foregoing aspects, the methods permit detection of microbial nucleic acids present in the original clinical samples at between 10 and 100,000 colony forming units/mL (cfu/mL), between 10 and 10,000 cfu/mL, or between 10 and 100 cfu/mL. In some embodiments of each of the foregoing aspects, the methods permit detection of microbial nucleic acids present in the clinical samples at between 2.5 and 100,000 cfu/mL, between 2.5 and 10,000 cfu/mL, between 2.5 and 1,000 cfu/mL, or between 2.5 and 100 cfu/mL.

In some embodiments of each of the foregoing aspects, the methods permit detection of microbial nucleic acids present in the clinical samples at between 1 and 100,000 cfu/mL, between 1 and 1,000 cfu/mL, between 1 and 100 cfu/mL, or between 1 and 10 cfu/mL.

DETAILED DESCRIPTION OF INVENTION

Figure 1:
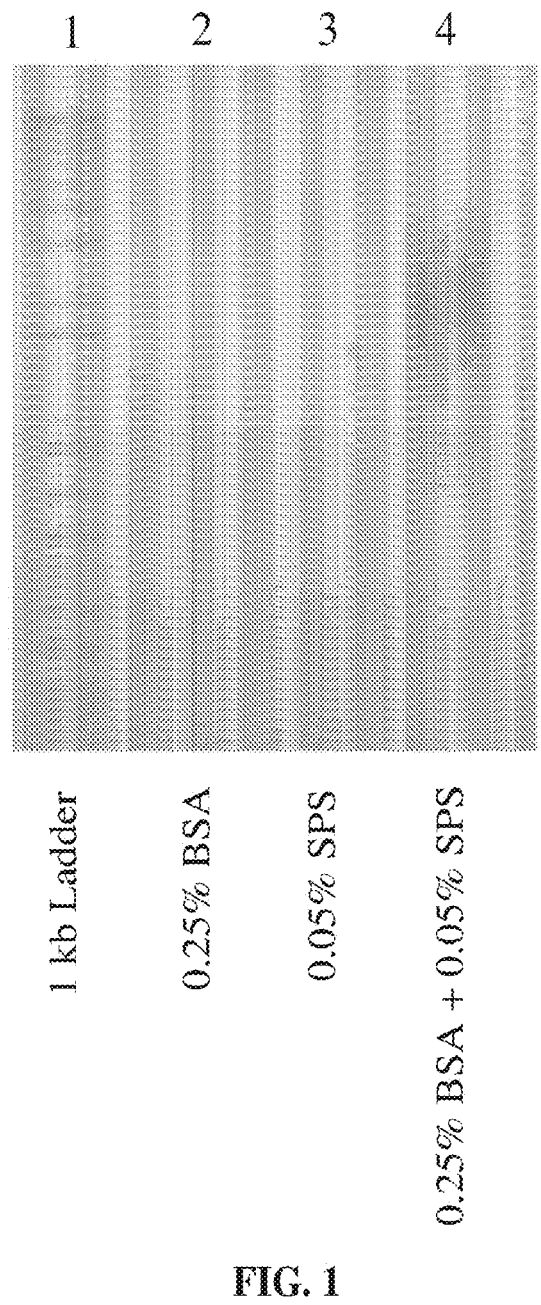
FIG. 1 illustrates that SPS forms large complexes with albumin, the most abundant protein in blood. The BSA-SPS complexes are visualized in an agarose gel stained with SYBR-Safe (ThermoFisher, Waltham, MA). Lane 1 is a 1 kb DNA ladder (Invitrogen, Carlsbad, CA); lane 2 is 0.25% BSA (Sigma-Aldrich, St. Louis, MO); lane 3 is 0.05% SPS; lane 4 is 0.25% SPS+0.05% BSA, forming a complex.

Clinical samples obtained from patients are critical in diagnosing a wide range of diseases and disorders. The ability to rapidly and efficiently prepare clinical samples for diagnostic testing is not only critical to maintaining patient health, but is also more cost-effective and efficient for both the doctor's office and laboratory that prepares the clinical sample and performs diagnostic testing.

Clinical blood samples are routinely obtained from patients having or suspected of having a pathogenic microbe infection. The use of additives such as sodium polyanethol sulfonate (SPS) and heparin in blood samples maintains bacterial viability, recovery, and the ability to rapidly identify the pathogenic microbe(s), and allows the doctor to more reliably predict which antimicrobial(s) will most effectively treat the infection (Belding and Kelbanoff, 1972, "Effect of Polyanetholsulfonate on Antimicrobial Systems in Blood," Appl. Microbiol. 24(5): 691-698). Identifying the pathogenic microbe(s) requires that the microbial nucleic acid be amplified relative to the subject's nucleic acid. Because in vitro amplification of nucleic acids is inhibited by the presence of nucleic acid amplification inhibitors in clinical samples, current practice is to either (1) avoid SPS containing samples all together, which decreases microbial recovery efficiency, or (2) culture the microbe in vivo, which has a significantly longer timeline (see, e.g., US 2018/0142231 A1).

The present disclosure is based, in part, on the discovery that polyanionic polymer nucleic acid amplification inhibitors can be removed from clinical samples during processing through the addition of a protease. These nucleic acid amplification inhibitors are non-protein compounds (e.g., polymers and organic compounds such as glycosaminoglycans) that, when present in clinical samples, block subsequent diagnostic testing such as microbe identification.

Definitions

All scientific and technical terms used herein, unless otherwise defined below, are intended to have the same meaning as commonly understood by one of ordinary skill in the art to which it belongs. In the case of any conflict, the present specification, including definitions, will control. References to techniques employed herein are intended to refer to the techniques as commonly understood in the art, including variations on those techniques or substitutions of equivalent or later-developed techniques which would be apparent to one of skill in the art. In order to more clearly and concisely describe the subject matter which is the invention, the following definitions are provided for certain terms which are used in the specification and appended claims.

As used herein, "preparing" refers to the steps performed to modify a clinical sample before diagnostic testing. In some embodiments, preparing comprises collecting, separating, removing a portion of the sample, and/or adding an additional component, such as a protease, to the sample.

As used herein, "separating" refers to physically partitioning a clinical sample into at least two distinct fractions.

As used herein, "host cells" refers to cells derived from the host or subject that are distinct from commensal (e.g., microbial cells which are part of the host microbiome), infectious (e.g., pathogenic microbes) or contaminating cells (e.g., introduced accidentally during sample collection or preparation). The term "host" may refer to a patient or medical subject, which may be a human or non-human mammal.

As used herein, "obtaining" refers to either withdrawing a clinical sample from a subject or receiving a clinical sample which has been withdrawn from a subject. Withdrawing a clinical sample from a subject may be accomplished by any route known in the art, including, but not limited to: intravenous, intra-arterial, intraperitoneal, intracranial, intra-spinal, intramuscular, intra-urethral, intra-tracheal, and intra-nasal. In various embodiments, "withdrawing" may be accomplished using a syringe, biopsy needle, aspiration tube, swab or similar devices, or by urination, defecation, expectoration, wound drainage or lavage.

As used herein, a "fraction" refers to a distinct sub-sample that has been physically separated from a larger and more complex sample. In some embodiments, a fraction comprises host cells, microbes, soluble proteins, and/or polyanionic polymer nucleic acid amplification inhibitors. Separation of a sample into two or more fractions need not be complete or perfect. For example, centrifugation of a whole blood sample into cell and plasma fractions will typically result in a cell fraction or pellet which nonetheless includes some plasma, and a plasma fraction or supernatant which nonetheless contains some cells. The degree or purity separation is within the control of a person of skill in the art, although perfect separation is neither practical nor necessary.

As used herein, "centrifugation" refers to the separation of a sample into components based upon density, wherein more dense components (e.g., blood cells, large particles, etc.) will form a pellet and less dense components (e.g., liquids, small peptides, etc.) will form a supernatant.

As used herein, "microfluidics" refers to separating a clinical sample into fractions by flowing the clinical sample through micro-channels. Microfluidic devices can separate different type of cells based upon cell size, isotachoporetic, optical, magnetic, and/or other biophysical properties that distinguish the cell types.

As used herein, "plasma tubes" refer to a container for isolating plasma. Plasma tubes can be used to isolate specific cell types (e.g., red blood cells, white blood cells, platelets, microbes) into various fractions.

As used herein, "immunoprecipitation" refers to the immobilization of specific cell types (e.g., red blood cells, white blood cells, platelets) or proteins using immunoglobulins or synthetic molecules derived-from or based-upon immunoglobulins (e.g., Fab fragments, F(ab')$_2$ fragments, Fab' fragments, Fd fragments, Fv fragments, and scFv fragments, as well as corresponding heavy chain-only antibodies (hcAb) and corresponding fragments from cartilaginous fish and camelid species). The immunoglobulin (or immunoglobulin-like) molecules can bind to any macromolecule (e.g., protein, glycoprotein) that distinguishes the cells or proteins to be separated.

As used herein, "filtration" refers to removing a structure from a clinical sample. A structure may be a cell, a cell fragment, organelle, microbe, large protein, or protein complex (e.g., polyanionic polymer nucleic acid amplification inhibitor and protein).

As used herein, "removing" a portion of the sample refers to withdrawing the majority of one portion of a sample, wherein the majority refers to at least 50%, but may include more than 60%, more than 70%, more than 80%, more than 90%, more than 95%, or more than 99% of the sample. Removing may be performed by any method known in the art, including but not limited to pipetting, decanting, and filtering. In some embodiments, removing a portion is by pipetting a liquid phase (e.g., supernatant).

As used herein, a "clinical sample" refers to a diagnostic specimen that is withdrawn, derived or otherwise obtained from a subject and processed for diagnostic testing. As used herein, clinical samples include blood, sputum, urine, mucus, saliva, tissue abscess, wound drainage, lymph, lavage, stool, cerebral spinal fluid or any fluid aspirate or tissue extraction of human and/or other mammalian origin (EEHealth, "Microbiology Collection", 2018).

As used herein, a "polyanionic polymer" is a non-proteinaceous substance with a molecular structure consisting of multiple similar chemical units bonded together and comprising multiple negatively-charged groups, and that has an average molecular weight of at least 500 daltons (500 Da).

As used herein, "sodium polyanethol sulfonate" (or "SPS") is a polyanionic polymer that is commonly utilized as an anticoagulant in vacuum liquid containers, including blood collection containers. SPS helps to preserve bacteria present in a clinical blood sample by inhibiting the complement cascade from killing the bacteria through innate and humoral immunity. Commercial SPS preparations typically have an average molecular weight of 9-11 kDa (e.g., Cat. No. 444464, Sigma-Aldrich, St. Louis, MO).

As used herein, "heparin" is a glycosaminoglycan comprising an unbranched polysaccharide consisting of repeating disaccharide units. Heparin is typically obtained from mucosal tissues of mammals (e.g., cattle lungs or pig intestines), but can be obtained from other tissues and from other mammals. Commercial heparin preparations typically have an average molecular weight of 12-15 kDa, but native heparin can range from 3-30 kDa. As used herein, the term "heparin" is intended to include any "heparin salt." A "heparin salt" is a compound in which heparin is combined with a positively charged molecule (e.g., sodium heparin, lithium heparin, or ammonium heparin).

As used herein, a "nucleic acid amplification inhibitor" refers to a compound that is added to a clinical sample to an unnatural level and that inhibits the activity of a DNA polymerase when present during a nucleic acid amplification reaction. In some embodiments, a nucleic acid amplification inhibitor is introduced into a clinical sample during sample collection. In some embodiments, a nucleic acid amplification inhibitor is introduced into a clinical sample during sample processing. A nucleic acid amplification inhibitor may be a natural (produced by nature) or synthetic (not produced by nature). A nucleic acid amplification inhibitor may be a non-natural non-protein such as SPS. A nucleic acid amplification inhibitor may be a natural non-protein such as heparin.

As used herein, "soluble" refers to the ability of a protein to remain in a solution rather than precipitating and/or forming an insoluble aggregate.

As used herein, "serum" refers to the blood component which comprises the blood plasma, all the electrolytes, antibodies, antigens, hormones, and any exogenous substances, such as drugs and microorganisms. Serum is not intended to include blood cells or platelets, although residual cells may be present after preparing serum.

As used herein, a "serum protein" refers to any protein in the blood plasma which is not involved in clotting (e.g., a fibrinogen). Serum proteins include, but are not limited to, albumins, such as human serum albumin, and globulins, such as alpha globulin, beta globulin, and gamma globulin, as well as transferrin, lactoferrin, globins, and antibodies.

As used herein, a "microbe" is a microorganism that requires a microscope to be visualized. Examples of microbes include bacteria, archaea, fungi, protists, viruses, and microscopic animals.

As used herein, a "pathogenic microbe" is a microbe that causes disease. The most common pathogenic microbes in humans are viruses and bacteria. Less common pathogenic microbes include fungi, protozoa, and helminths.

As used herein, a "protease" refers to an enzyme that breaks down proteins and peptides through hydrolysis of peptide bonds.

As used herein, a "container" is a vessel for collecting a clinical sample from a subject. In some embodiments, the subject has or is suspected of having a microbial infection. In some embodiments of the present disclosure, a container is a vacuum liquid container (e.g., a Vacutainer®, BD Biosciences, Franklin Lakes, NJ). In some embodiments, a container is a blood culture bottle.

As used herein, a "vacuum liquid container" is a sterile glass or plastic sample collection tube comprising a rubber stopper which maintains a vacuum seal inside of the tube. This vacuum seal facilitates the collection of a predetermined volume of liquid. In some embodiments of the present disclosure, a vacuum liquid container contains sodium polyantheol sulfonate (SPS). In some embodiments, a vacuum liquid container contains heparin.

As used herein, a "blood culture bottle" is a sterile glass or plastic blood collection container which is utilized to collect and culture a clinical sample from a patient having or suspected of having a bacterial infection. Blood culture bottles facilitate the growth of microbes in the clinical sample for downstream identification of the microbial species present. In some embodiments of the present disclosure, a blood culture bottle comprises sodium polyanethol sulfonate (SPS). In some embodiments, a blood culture bottle comprises heparin.

As used herein, "nucleic acid amplification" refers to a process for amplifying or multiplying a specific population or populations of nucleic acid molecules from a clinical blood sample. In some embodiments, the population is from a pathogen, such as virus or bacterium. In some embodiments, the population is from the host of clinical blood sample. The amount of nucleic acid molecules in the population can be expanded in any of several ways, including polymerase chain reaction (PCR), strand displacement amplification (SDA), or transcription mediated amplification (TMA). In some embodiments, nucleic acid amplification is isothermal strand-displacement amplification, PCR, qPCR, RT-PCR, degenerate oligonucleotide PCR, or primer extension pre-amplification.

As used herein, a "polymerase" refers to an enzyme which catalyzes the formation of a new nucleic acid molecule (e.g., DNA or RNA) utilizing an existing nucleic acid molecule (e.g., DNA or RNA) as a template to produce a complementary (or substantially complementary) polynucleotide sequence in the new molecule. In some embodiments, a polymerase is a strand displacement polymerase, which catalyzes the displacement of one strand of a DNA double helix before DNA or RNA synthesis occurs. In some embodiments, a strand displacement polymerase is phi29 DNA polymerase (e.g., Cat. No. M0269, New England BioLabs, Ipswich, MA), Bst DNA polymerase Large Fragment (e.g., Cat. No. M0275, New England BioLabs, Ipswich, MA), or DNA polymerase I Klenow Fragment (e.g., Cat. No. M0210, New England BioLabs, Ipswich, MA).

PRINCIPLES OF THE INVENTION

The present invention depends, in part, upon the discovery that polyanionic polymer nucleic acid amplification inhibitors (e.g., SPS, heparin, hyaluronate, dermatan sulfate polyanion, and chondroitin D-glucuronate anion) can be removed from clinical samples by adding proteases. This is polyanionic polymer nucleic acid amplification inhibitors bind naturally-occurring proteins that are present in clinical samples during nucleic acid amplification. Thus, the present disclosure provides methods to remove polyanionic polymer nucleic acid amplification inhibitors from clinical samples obtained from subjects infected with pathogenic microbes.

Clinical Samples.

The methods of the invention can be practiced on a variety of types of clinical samples obtained from a variety of types of subjects. In some embodiments, a clinical sample is blood, lymph, urine, stool, sputum, mucus, saliva, tissue abscess, wound drainage, lavage, cerebral spinal fluid or any fluid aspirate or tissue extraction of human and/or other mammalian origin.

Sample Containers

A variety of different sample containers are used in the art, adapted to different types of clinical samples. In many cases, the most commonly used and commercially available sample containers are pre-loaded with preservatives and/or anticoagulants (e.g., SPS, heparin, hyaluronate, dermatan sulfate polyanion, EDTA, and chondroitin D-glucuronate anion) that may have the unintended effect of acting as nucleic acid amplification inhibitors during genetic identification or analysis of the different nucleic acids present in a sample. For example, commonly used blood collection containers, blood culture bottles, plasma tubes, and blood culture media may include heparin (e.g., Cat. Nos. 364960, 366667, 367871, 367878, 367884, 367886, 367960, 367961, 367962, and 367964 Vacutainer® collection tubes, BD Biosciences, Franklin Lakes, NJ), SPS (e.g., Cat. No. 364960 Vacutainer® collection tubes, Cat. Nos. 442022 and 442023, BACTEC™ PLUS media, BD Biosciences, Franklin Lakes, NJ) or potassium EDTA (e.g., Cat. Nos. 367842, 367899 and 368589, Vacutainer® Plus Plastic K₂EDTA Tubes, BD Biosciences, Franklin Lakes, NJ).

In the methods of the present invention, the samples are typically removed from the sample containers in which they were collected and transferred to a new container (e.g., a centrifugation tube or microfluidic device) prior to practicing the methods of the invention. In some cases, however, depending upon the nature of the sample collection container, one or more steps may be performed in the container into which the samples were collected.

Proteins Binding Polyanionic Polymer Nucleic Acid Amplification Inhibitors

As described above, the invention depends, in part, upon the discovery that adding proteases to clinical samples reduces contamination by certain nucleic acid amplification inhibitors in processed clinical samples, without otherwise substantially harming the integrity or quality of the samples, and thereby improves nucleic acid amplification of nucleic acids within the sample. Without being bound by any particular theory, it is believed that certain proteins in clinical samples can bind to certain nucleic acid amplification inhibitors to form complexes such that the nucleic acid amplification inhibitors and proteins remain in the same fraction during processing of the sample. This can have an adverse effect if it prevents separation of the nucleic acid amplification inhibitors from the population of nucleic acids to be amplified.

In some embodiments, the proteins which bind to the nucleic acid amplification inhibitors are soluble in physiological fluids and/or solutions used in processing (e.g., supernatants from centrifugation or solutions used in microfluidic devices or filtration). For example, in some embodiments, the protein may be a soluble serum protein, such as serum albumin. In some embodiments, the protein may be any other soluble protein which forms a complex with a polyanionic polymer nucleic acid amplification inhibitor. Non-limiting examples of proteins in a clinical sample include human serum albumin, amylase, immunoglobulins, lactoferrin, calprotectin, myeloperoxidase, azurocidin, lactotransferrin, cathelicidin, lactase, myoglobin, hemoglobin, and transferrin.

Pathogenic Microbes.

In some aspects, the present disclosure provides methods for amplifying microbial DNA from a clinical sample following treatment of the clinical sample with a protease.

In some embodiments, the microbes are bacteria. Although bacteria are normally present in healthy mammals, disruption of the balance amongst different types of bacteria within a host, disruption of the balance between the bacteria and the host, or the presence of pathogenic bacteria within the host can lead to infection. Non-limiting examples of pathogenic bacteria include: *Staphylococcus aureus* (*S. aureus*), *Staphylococcus epidermidis* (*S. epidermidis*), *Streptococcus agalactiae* (*S. agalactiae*), *Enterococcus faecalis* (*E. faecalis*), *Enterococcus faecium* (*E. faecium*), *Escherichia coli* (*E. coli*), *Klebsiella pneumoniae* (*K. pneumoniae*).

*S. aureus* is a bacterium that is normally present in the human body and is frequently found in the nose, respiratory tract, and on the skin. Although *S. aureus* is not always pathogenic, it is a common cause of skin infections including abscesses, respiratory infections, and food poisoning. The common method of treating *S. aureus* infections is using antibiotics, although the emergence of antibiotic-resistant strains of *S. aureus* such as methicillin-resistance *S. aureus* (MRSA) and vancomycin-resistant *S. aureus* (VRSA) have become worldwide clinical health challenges.

*S. epidermidis* is a bacterium that is normally present in the human body, where it is frequently found on the skin. Although *S. epidermidis* is not generally pathogenic, subjects with compromised immune systems are at risk of developing *S. epidermidis* infections, and *S. epidermidis* poses a particular threat to subject with surgical implants because it can grow on plastic surfaces and spread to the human body. *S. epidermidis* strains are often resistant to antibiotics, including rifamycin, fluoroquinolones, gentamicin, tetracycline, clindamycin, and sulfonamides.

*S. agalactiae* is a bacterium that is generally not pathogenic and can be found in the gastrointestinal and genitourinary tract in up to 30% of humans. Pathogenic infections due to *S. agalactiae* are of concern for neonates and immunocompromised individuals. *S. agalactiae* infections in adults can be life-threatening and include bacteremia, soft-tissue infections, osteomyelitis, endocarditis, and meningitis. *S. agalactiae* is increasingly resistant to clindamycin and erythromycin.

*E. faecalis* is a bacterium that inhabits the gastrointestinal tracts of humans and other mammals. However, *E. faecalis* can cause endocarditis, septicemia, urinary tract infections, and meningitis. *E. faecalis* infections can be life-threatening, particularly when the *E. faecalis* is resistant to treatment with gentamicin and vancomycin.

*E. coli* is a bacterium that inhabits the gastrointestinal tracts of humans and other mammals, but it may also be pathogenic, resulting in conditions such as gastroenteritis, urinary tract infections, neonatal meningitis, hemorrhagic colitis, and bacteremia. *E. coli* is increasingly resistant to multiple antibiotics, including fluoroquinolones, cephalosporins, and carbapenems.

*K. pneumoniae* is a bacterium that is normally found in the mouth, skin, and intestines of humans and other mammals. However, it can cause destructive changes to human and mammal lungs if inhaled, particularly to alveoli. *K. pneumoniae* infections are generally seen in subjects with a compromised immune system, including subjects with diabetes, alcoholism, cancer, liver disease, chronic obstructive pulmonary diseases, glucocorticoid therapy, and renal failure. *K. pneumoniae* is increasingly resistant to multiple antibiotics, including fluoroquinolones, cephalosporins, tetracycline, chloramphenicol, carbapenem, and trimethoprim/sulfamethoxazole.

Methods for Isolating Nucleic Acids in a Clinical Sample.

In one aspect, the present disclosure provides a method for preparing a clinical sample from a subject containing cells from the subject, microbes, and at least one polyanionic polymer nucleic acid amplification inhibitor that binds to at least one protein in the sample comprising the steps of: (a) obtaining the clinical sample from the subject comprising cells from the subject, the microbes, the protein, and the polyanionic polymer nucleic acid amplification inhibitor; (b) separating the clinical sample into a first fraction comprising the cells of the subject and a second fraction comprising the microbes and the polyanionic polymer nucleic acid amplification inhibitor bound to the protein; (c) adding to the second fraction a protease which degrades the protein; and (d) separating the second fraction into a third fraction comprising the microbes and (ii) a fourth fraction comprising the polyanionic polymer nucleic acid amplification inhibitor.

In another aspect, the present disclosure provides methods for preparing a clinical sample from a subject comprising microbes, and at least one polyanionic polymer nucleic acid amplification inhibitor that binds at least one protein in the sample, comprising the steps of: (a) obtaining the clinical sample from the subject comprising the microbes and at least one polyanionic polymer nucleic acid amplification inhibitor, (b) adding to the sample a protease which degrades the protein, (c) separating the sample into a first fraction comprising the cells of the subject and a second fraction comprising the microbes and the polyanionic polymer nucleic acid amplification inhibitor bound to the protein, (d) removing the second fraction from the first fraction, and (e) separating the second fraction into a third fraction comprising the microbes and a fourth fraction comprising the polyanionic polymer nucleic acid amplification inhibitor.

Nucleic Acid Amplification Inhibitors.

In some embodiments, a nucleic acid amplification inhibitor is present in the container when the clinical sample is obtained. In some embodiments, the nucleic acid amplification inhibitor is introduced into a clinical blood sample during sample processing. A nucleic acid amplification inhibitor may be a polyanionic polymer compound, such as sodium polyanethol sulfonate (SPS) or heparin. A nucleic acid amplification inhibitor may also be a protein, such as a bacterial toxin or immunoglobulin (e.g., IgG).

In some embodiments, a nucleic acid amplification inhibitor is a polyanionic polymer. In some embodiments, a polyanionic polymer nucleic acid amplification inhibitor has an average molecular weight greater than 500 Da, greater than 1 kilodaltons (1 kDa), greater than 2 kDa, greater than 3 kDa, greater than 4 kDa, greater than 5 kDa, greater than 6 kDa, greater than 7 kDa, greater than 8 kDa, greater than 9 kDa, or greater than 10 kDa. Non-limiting examples of polyanionic polymers include sodium polyanethol sulfonate, heparin, hyaluronate, dermatan sulfate polyanion, and chondroitin D-glucuronate anion.

In some embodiments, the at least one polyanionic polymer is sodium polyanethol sulfonate. As noted above, SPS is added to various commercially available sample collection containers, including blood culture bottles and microbiological blood collection vacuum liquid containers. SPS interferes with the activity and efficacy of cationic antimicrobials and counteracts the inhibitory effects of blood against bacteria. However, the presence of SPS in clinical sample containers results in the inhibition of downstream molecular-based assays, including assays using polymerase chain reaction (PCR) amplification of nucleic acids. SPS also preserves bacteria present in a clinical blood sample by inhibiting the complement cascade from killing the bacteria through innate and humoral immunity.

In some embodiments, the polyanionic polymer nucleic acid amplification inhibitor is heparin. Heparin is an anticoagulant that activates antithrombins, thus blocking the coagulation cascade. As noted above, heparin is present in some sample collection containers, including clinical blood sample containers. In some embodiments, the heparin is lyophilized. In some embodiments, the heparin is spray-dried. Typically, either heparin or another anticoagulant is present in blood sample containers intended for the collection of whole and plasma because the anticoagulant can prevent formation of clotted blood and serum. Conversely, anticoagulants such as heparin are typically absent in blood sample collection containers to be used for clotted blood and serum. In some embodiments, the heparin that is in a clinical blood sample container is a heparin salt. In some embodiments, heparin is sodium heparin. In some embodiments, heparin is lithium heparin. In some embodiments, heparin is ammonium heparin.

Proteases.

The present disclosure provides methods for preparing a clinical sample, the methods comprising adding to the clinical sample a protease. Non-limiting examples of proteases useful in the invention include proteinase K, Factor Za, Arg-C proteinase, Asp-N endopeptidase, Asp-N endopeptidase+N-terminal Glu, BNPS-Skatole, Caspase1, Chymotrypsin-high specificity, Clostripain, CNBr, Enterokinase, Granzyme B, formic acid, glutamyl endopeptidase, hydroxylamine, iodosobenzoic acid, LysC, LysN, NTCB, pepsin, proline-endopeptidase, staphylococcal peptidase I, tobacco etch virus protease, thermolysin, thrombin, trypsin, elastase, plasmin, acrosomal protease, complement Cl, keratinase, collagenase, fibrinolysin, cocoonase, thermolysin, and carboxypeptidase A.

In some embodiments, the protease is proteinase K. Proteinase K is an enzyme produced by the fungus Engyodontium album. Proteinase K preferentially digests proteins after hydrophobic amino acids (e.g., glycine, alanine, valine, leucine, isoleucine, proline, phenylalanine, methionine, or tryptophan). However, proteins will be completely degraded if incubated with proteinase K for long enough. Proteinase K activity is stable over a wide pH range (e.g., pH 4-pH 12), and an elevation of the reaction temperature from 37° C. to 50-60° C. may increase in the activity of proteinase K by several-fold. The addition of proteinase K to samples with nucleic acids rapidly inactivates proteins that bind and degrade the nucleic acids.

In some embodiments, the protease is selected from the group consisting of: proteinase K, Factor Za, Arg-C proteinase, Asp-N endopeptidase, Asp-N endopeptidase+N-terminal Glu, BNPS-Skatole, Caspase1, Chymotrypsin-high specificity, Clostripain, CNBr, Enterokinase, Granzyme B, formic acid, glutamyl endopeptidase, hydroxylamine, iodosobenzoic acid, LysC, LysN, NTCB, pepsin, proline-endopeptidase, staphylococcal peptidase I, tobacco etch virus protease, thermolysin, thrombin, and trypsin.

In some embodiments, the amount of protease added is between 5 units/mL (U/mL) and 5000 U/mL. A "protease unit" (U) is an international unit of a protease's catalytic activity, defined as the amount of the enzyme that catalyzes the conversion of 1 micromole of substrate per minute (1 U=1 μmol/min) under the specified conditions of an accepted assay method. In some embodiments, the amount of protease added is at least 5 U/mL. In some embodiments, the amount of protease added is less than or equal to 5000 U/mL. In some embodiments, the amount of protease added is 5 U/mL, 100 U/mL, 200 U/mL, 300 U/mL, 400 U/mL, 500 U/mL, 600 U/mL, 700 U/mL, 800 U/mL, 900 U/mL, 1000 U/mL, 1100 U/mL, 1200 U/mL, 1300 U/mL, 1400 U/mL, 1500 U/mL, 1600 U/mL, 1700 U/mL, 1800 U/mL, 1900 U/mL, 2000 U/mL, 2100 U/mL, 2200 U/mL, 2300 U/mL, 2400 U/mL, 2500 U/mL, 2600 U/mL, 2700 U/mL, 2800 U/mL, 2900 U/mL, 3000 U/mL, 3100 U/mL, 3200 U/mL, 3300 U/mL, 3400 U/mL, 3500 U/mL, 3600 U/mL, 3700 U/mL, 3800 U/mL, 3900 U/mL, 4000 U/mL, 4100 U/mL, 4200 U/mL, 4300 U/mL, 4400 U/mL, 4500 U/mL, 4600 U/mL, 4700 U/mL, 4800 U/mL, 4900 U/mL, or 5000 U/mL.

In some embodiments, the protease is incubated with the sample (or fraction of the sample) at between 20° C. and 60° C. In some embodiments, the protease is incubated at least 20° C. In some embodiments, the protease is incubated at less than or equal to 60° C. In some embodiments, the protease is incubated at 20° C., 25° C., 30° C., 35° C., 40° C., 45° C., 50° C., 55° C., or 60° C.

In some embodiments, the protease is incubated with the sample (or fraction of the sample) for between 10 minutes and 120 minutes. In some embodiments, the protease is incubated for at least 10 minutes. In some embodiments, the protease is incubated for less than or equal to 120 minutes. In some embodiments, the protease is incubated for 10 minutes, 20 minutes, 30 minutes, 40 minutes, 50 minutes, 60 minutes, 70 minutes, 80 minutes, 90 minutes, 100 minutes, 110 minutes, or 120 minutes.

Clinical Sample Preparation

In some aspects, the present disclosure provides methods for preparing clinical samples. "Preparing" refers to the steps performed to modify a clinical sample before diagnostic testing. In some embodiments, preparing comprises obtaining, separating the clinical sample, removing a portion of the sample, and/or adding an additional component, such as a protease, to the sample.

The methods of the invention include separating or partitioning a sample (or subsample) into fractions comprising host cells, microbes, and/or polyanionic polymer nucleic acid amplification inhibitors. Non-limiting methods of separation include centrifugation, microfluidics, immunoprecipitation, and filtration.

In various embodiments, the host cells can be red blood cells, white blood cells, platelets, epithelial cells, muscle cells, bone cells, neurons, glial cells, hepatocytes, immune cells, renal cells, gastric cells, and/or colonic cells.

In some embodiments, the methods include multiple steps of centrifugation. In some embodiments, there are 2 steps of centrifugation. In some embodiments, there are 3 steps of centrifugation. In some embodiments, there are 4 steps of centrifugation. In some embodiments, there are 5 steps of centrifugation. In some embodiments, multiple steps of centrifugation may be performed at the same speed and/or for the same length of time. In some embodiments, multiple steps of centrifugation may be performed at different speeds and/or for different lengths of time.

In some embodiments, a sample (or sample fraction) is centrifuged at between 500×g (500×force of gravity) and 50,000×g. In some embodiments, a sample (or sample fraction) is centrifuged at least 500×g. In some embodiments, a sample (or sample fraction) is centrifuged at less than or equal to 50,000×g. In some embodiments, a sample (or sample fraction) is centrifuged at 500×g, 1,000×g, 2,000×g, 3,000×g, 4,000×g, 5,000×g, 6,000×g, 7,000×g, 8,000×g, 9,000×g, 10,000×g, 11,000×g, 12,000×g, 13,000×g, 14,000×g, 15,000×g, 16,000×g, 17,000×g, 18,000×g, 19,000×g, or 20,000×g.

In some embodiments, a sample (or sample fraction) is centrifuged for between 2 minutes and 60 minutes. In some embodiments, a sample (or sample fraction) is centrifuged for at least 2 minutes. In some embodiments, a sample (or sample fraction) is centrifuged for less than or equal to 60 minutes. In some embodiments, a sample (or sample fraction) is centrifuged for 2 minutes, 5 minutes, 10 minutes, 15 minutes, 20 minutes, 25 minutes, 30 minutes, 35 minutes, 40 minutes, 45 minutes, 50 minutes, 55 minutes, or 60 minutes.

In some embodiments, centrifugation is performed using a vacuum liquid container. In some embodiments, centrifugation is performed using a plasma tube. Plasma tubes contain an anti-coagulant (e.g., EDTA, sodium-citrate, heparin) for separating plasma from serum.

As described above, sample separation can be performed using microfluidic devices known in the art. Non-limiting examples of microfluidic devices include inertial microfluidics (Hou et al., 2015, "Direct detection and drug-resistance profiling of bacteremias using inertial microfluidics," Lab Chip, 15(10): 2297-2307), plug-based microfluidics (Boedicker et al., 2008, "Detecting bacteria and determining their susceptibility to antibiotics by stochastic confinement in nanoliter droplets using plug-based microfluidics," Lab Chip, 8: 1265-1272), on-chip bacterial purification (Mahalanabis et al., 2009, "Cell lysis and DNA extraction of gram-positive and gram-negative bacteria from whole blood in a disposable microfluidic chip," Lab on a Chip 9: 2811-2817; Cady et al., 2005, Sensors and Actuators B: Chemical, 107: 332-341.), and affinity-based capture (Boehm et al., 2007, Sensors and Actuators B: Chemical, 126: 508-514; Xia et al., 2006, "Combined microfluidic-micromagnetic separation of living cells in continuous flow," Biomedical Microdevices 8: 299-308; Yung et al., 2009, "Micromagnetic-microfluidic blood cleansing device," Lab on a Chip, 9:1171-1177; Lee et al., 2014, "Synthetic ligand-coated magnetic nanoparticles for microfluidic bacterial separation from blood," Nano Letter, 14: 1-5; Cho et al., 2007, "One-step pathogen specific DNA extraction from whole blood on a centrifugal microfluidic device," Lab on a Chip, 7: 565-573).

In some embodiments, a clinical sample is separated into one or more fractions using microfluidics. In some embodiments, macromolecular complexes of proteins, polyanionic polymer nucleic acid amplification inhibitors, and/or host cells are separated by microfluidics into one fraction. In some embodiments, microbes and/or host cells are separated by microfluidics into one fraction. Macromolecular complexes, host cells or microbes may be labeled to aid in separation. In some embodiments, the macromolecular complexes, host cells or microbes are labeled with a fluorophore (e.g., GFP, YFP), an affinity tag, or an antibody that binds to a protein on the surface of the protein and/or microbe. In some embodiments, the macromolecular complexes, host cells or microbes are not labeled prior to separation. Methods of separating non-labeled macromolecular complexes, host cells and/or microbes in a clinical sample by microfluidics include, but are not limited to, size-exclusion and isotachoporesis. Size-exclusion microfluidics separates smaller particles (e.g., microbes, proteins, polyanionic polymers) from larger macromolecular particles (e.g., mammalian cells).

In some embodiments, a clinical sample is separated into one or more fractions using immunoprecipitation. Treatment of a clinical sample with a protease (e.g., Proteinase K) may decrease non-specific binding of proteins to antibodies during immunoprecipitation by preventing polyanionic polymer nucleic acid amplification inhibitors from forming a complex with proteins in the clinical sample that may non-specifically bind to immunoprecipitation antibodies. In some embodiments, a clinical sample is treated with a protease before immunoprecipitation to decrease the retention of polyanionic polymer nucleic acid amplification inhibitors.

Immunoprecipitation may utilize antibodies that bind proteins on microbes, but not eukaryotic cells. Immunoprecipitation may utilize antibodies that bind proteins on eukaryotic cells, but not microbes. In some embodiments, immunoprecipitation enriches a clinical sample in host cells by binding to and removing microbe cells. In some embodiments, immunoprecipitation depletes a clinical sample of host cells by binding to and removing host cells.

Immunoprecipitation may be utilized in conjunction with another means of separating a clinical sample. In some embodiments, samples that are centrifuged are also separated by immunoprecipitation to further decrease the retention of polyanionic polymer nucleic acid inhibitors. In some embodiments, samples that are separated by microfluidics are also separated by immunoprecipitation to further decrease retention the retention of polyanionic polymer nucleic acid inhibitors. In some embodiments, samples that are separated by filtration are also separated by immunoprecipitation to further decrease retention the retention of polyanionic polymer nucleic acid inhibitors.

In some embodiments, a clinical sample is separated into one or more fractions using filtration. Depending upon the pore size of a filter, the filter can remove host cells, microbes, or protein complexes (e.g., polyanionic polymer nucleic acid amplification inhibitors bound to proteins).

In the methods of the invention, a protease is added to a clinical sample or a fraction of the sample during sample preparation. In some embodiments, the protease is added to a clinical sample before any separation of the sample into fractions. In some embodiments, the protease is added to a fraction (e.g., a supernatant, resuspended pellet, filtrate) after one or more steps of separation into fractions.

Amplification of Nucleic Acids.

In some aspects, the present invention includes an additional step of amplification of a population of nucleic acid that were present in the original sample. Amplification of a nucleic acid population can be performed prior to identification of the source of nucleic acids (e.g., mammalian DNA, microbe DNA). In some embodiments, the nucleic acids that are amplified are microbial nucleic acids. In some embodiments, the nucleic acids that are amplified are host nucleic acids. In some embodiments, the nucleic acids are DNA. In some embodiments, the nucleic acids are RNA. Non-limiting examples of nucleic acid amplification techniques known in the art include: polymerase chain reaction (PCR), quantitative PCR (qPCR), reverse-transcriptase PCR (RT-PCR), degenerate oligonucleotide PCR, primer extension pre-amplification, strand-displacement amplification (SDA), or transcription mediated amplification (TMA). In some embodiments, the nucleic acid amplification is by isothermal strand-displacement amplification, polymerase chain reaction (PCR), quantitative PCR (qPCR), real-time PCR (RT-PCR), degenerate oligonucleotide PCR, or primer extension pre-amplification.

Amplification of a population of nucleic acids by any of the previously-mentioned methods requires a primer and a polymerase. Non-limiting examples of polymerases include eukaryotic polymerases such as polymerase alpha, polymerase delta, and polymerase epsilon; bacterial polymerases such as *Thermus aquaticus* (Taq), Deep Vent® (New England BioLabs, Ipswich, MA), and Therminator™ (New England BioLabs, Ipswich, MA); RNA polymerases such as RNA polymerase I and RNA polymerase II; and strand-displacing polymerases.

In some embodiments, the nucleic acid amplification is by a strand-displacement polymerase. A "strand-displacement polymerase" is an enzyme which separates the strands of DNA double helix as it extends a primer template. Non-limiting examples of strand-displacement polymerases include phi29 DNA polymerase; Bst DNA polymerase, Large Fragment (New England BioLabs, Ipswich, MA); Bsu DNA polymerase, Large Fragment (New England BioLabs, Ipswich, MA); Deep Vent® DNA polymerase (New England BioLabs, Ipswich, MA); Deep Vent® (exo) DNA polymerase (New England BioLabs, Ipswich, MA); DNA polymerase I, large fragment; M-MuLV reverse transcriptase; Therminator® DNA polymerase (New England BioLabs, Ipswich, MA); Vent® DNA polymerase (New England BioLabs, Ipswich, MA); Vent® (exo) DNA polymerase (New England BioLabs, Ipswich, MA); SD polymerase; and Klenow Fragment. In some embodiments, the nucleic acid amplification is by phi29 DNA polymerase, Bst DNA polymerase, Large Fragment, or Klenow Fragment. As used herein, "phi29" refers to the replicative polymerase from the *Bacillus subtilis* phage phi29. The phi29 polymerase has strand displacement and processive synthesis properties, as well as an inherent $3' \rightarrow 5'$ exonuclease proofreading ability.

In the methods of the invention, addition of a protease increases the amplification of nucleic acid in a clinical sample. In some embodiments, the nucleic acid population is microbial nucleic acid. In some embodiments, the addition of a protease increases the amplification of nucleic acid by between 5-fold and 100-fold compared with samples not treated with protease. In some embodiments, the amplification of nucleic acid is increased by 5-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold compared with samples not treated with protease. In some embodiments, the amplification of nucleic acid is increased by at least 5-fold compared with samples not treated with protease. In some embodiments, the amplification of nucleic acid is increased by less than 100-fold compared with samples not treated with protease.

In the methods of the invention, addition of a protease increases the isolation of nucleic acid from a clinical sample. In some embodiments, the nucleic acid is a microbial nucleic acid. In some embodiments, the addition of a protease increases the isolation of nucleic acid by between 10-fold and 100-fold, compared with samples not treated with protease. In some embodiments, the isolation of nucleic acid is increased by 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold compared with samples not treated with protease. In some embodiments, the isolation of nucleic acid is increased by at least 10-fold compared with samples not treated with protease. In some embodiments, the isolation of nucleic acid is increased by less than 100-fold compared with samples not treated with protease.

Applications to Alternative Methods of Sample Processing.

In some aspects, the present disclosure provides a method for preparing a clinical sample from a subject comprising microbes, cells, and at least one polyanionic polymer nucleic acid amplification inhibitor that binds at least one protein in the sample, comprising the steps of: (a) obtaining the clinical sample from the subject comprising the microbes, the protein and the polyanionic polymer nucleic acid amplification inhibitor, (b) adding to the clinical sample a protease which degrades the protein, (c) separating the clinical sample into a first fraction comprising the cells of the subject and a second fraction comprising the microbes and the polyanionic polymer nucleic acid amplification inhibitor bound to the protein, (d) removing the second fraction from the first fraction, (e) separating the second fraction into: a third fraction comprising the microbes and a fourth fraction comprising the polyanionic polymer nucleic acid amplification inhibitor.

In some aspects, the present disclosure provides a method for preparing a clinical sample from a subject comprising microbes, cells, and at least one polyanionic polymer nucleic acid amplification inhibitor that binds at least one protein in the sample, comprising the steps of: (a) obtaining the clinical sample from the subject comprising the microbes, the protein, and the polyanionic polymer nucleic acid amplification inhibitor, (b) separating the clinical sample into: a first fraction comprising the cells of the subject and a second fraction comprising the microbes and the polyanionic polymer nucleic acid amplification inhibitor bound to the protein (c) removing the second fraction from the first fraction, (d) adding to the second fraction a protease which degrades the protein in the second fraction after step (b) or step (c), (e) separating the second fraction into a third fraction comprising the microbes and a fourth fraction comprising the polyanionic polymer nucleic acid amplification inhibitor.

In some aspects, the present disclosure provides a method for preparing a clinical sample from a subject comprising microbes, and at least one polyanionic polymer nucleic acid amplification inhibitor that binds at least one protein in the sample, comprising the steps of: (a) obtaining the clinical sample from the subject comprising the microbes, the protein, and the polyanionic polymer nucleic acid amplification inhibitor, (b) selectively lysing the microbes, (c) adding to the clinical sample a protease which degrades the protein, (d) separating the clinical sample into a first fraction comprising the cells of the clinical sample and a second fraction comprising nucleic acid from the microbes.

In some embodiments of each of the foregoing aspects, the separating is by centrifugation. In some embodiments of each of the foregoing aspects, the separation is by filtration. In some embodiments of each of the foregoing aspects, the separation is by microfluidic size exclusion. In some embodiments of each of the foregoing aspects, the separation is by plasma tubes. In some embodiments of each of the foregoing aspects, the separating is by immunoprecipitation.

In some embodiments of each of the foregoing aspects, the clinical sample is blood, sputum, urine, mucus, saliva tissue abscess, wound drainage, lymph, lavage, stool, cerebral spinal fluid, or any fluid aspirate or tissue extraction of human or other mammalian origin.

In some embodiments of each of the foregoing aspects, the at least one polyanionic polymer nucleic acid amplification inhibitor is sodium polyanethol sulfonate. In some embodiments of each of the foregoing aspects, the at least one polyanionic polymer nucleic acid amplification inhibitor is heparin.

In some embodiments of each of the foregoing aspects, the obtaining step utilizes a vacuum liquid container or blood culture bottle.

In some embodiments of each of the foregoing aspects, the protease is selected from the group consisting of: proteinase K, Factor Xa, Arg-C proteinase, Asp-N endopeptidase, Asp-N endopeptidase+N-terminal Glu, 3-Bromo-3-methyl-2-(2-nitropheylthio)-3H-indole (BNPS-Skatole), Caspase1, Chymotrypsin-high specificity, Clostripain, cyanogen bromide (CNBr), Enterokinase, Granzyme B, formic acid, glutamyl endopeptidase, hydroxylamine, iodosobenzoic acid, LysC, LysN, 2-nitro-5-thiocyanatobenzoic acid (NTCB), pepsin, proline-endopeptidase, staphylococcal peptidase I, tobacco etch virus protease, thermolysin, thrombin, and trypsin.

In some embodiments of each of the foregoing aspects, the amount of protease added is between 5 units/mL (U/mL) and 5000 units/mL (U/mL).

In some embodiments of each of the foregoing aspects, the protease and the second fraction are incubated at between 20° C. and 55° C. for at least 10 minutes.

In some embodiments of each of the foregoing aspects, the microbe is a pathogenic microbe.

In some embodiments of each of the foregoing aspects, the method further comprises the step of nucleic acid amplification of nucleic acids in the third fraction. In some embodiments of each of the foregoing aspects, the nucleic acid amplification is isothermal strand-displacement amplification, polymerase chain reaction (PCR), quantitative PCR (qPCR), reverse transcriptase PCR (RT-PCR), degenerate oligonucleotide PCR, or primer extension pre-amplification.

In some embodiments of each of the foregoing aspects, the addition of the protease increases the amplification of microbial nucleic acid by at least 5-fold relative to samples in which protease has not been added.

EXAMPLES

Example 1: Sodium Polyanethol Sulfonate (SPS) Binds Serum/Plasma Proteins

Blood collection containers commonly contain the anticoagulant sodium polyanethol sulfonate (SPS). Although SPS has many advantages—prevention of the lysis of bacterial cells by the complement system, reduction of blood cell clumping, and facilitation of the separation of blood components into solids (e.g., red blood cells and white blood cells, etc.) and liquids (e.g., plasma, small molecular weight nucleic acid amplification inhibitors, etc.), it persistance in the liquid phase is widely known to inhibit downstream processes such as nucleic acid amplification.

One hypothesis for how SPS persists following the separation of blood into cells and plasma is that it forms a large complex with a molecule (e.g., a protein such as albumin, which is the most abundant protein in plasma and serum) in the liquid phase causing it to coprecipitate during the separation. This hypothesis was tested by pre-mixing 0.05% SPS with 0.25% bovine serum albumin (BSA) (Sigma-Aldrich, St. Louis, MO). The SPS-BSA mixtures were then separated by size on an agarose gel stained with SYBR-safe (ThermoFisher, Waltham, MA) (FIG. 1).

In FIG. 1, lane 1 is a 1 kb DNA ladder, lane 2 is 0.25% BSA, lane 3 is 0.05% SPS; lane 4 is a mixture of 0.25% SPS and 0.05% BSA. Solutions of 0.05% SPS and 0.25% BSA alone are not visible with SYBR-safe, indicating that SPS and BSA form a large macromolecular complex.

Example 2: SPS Protein Complexes are Reduced with Proteinase K Treatment

To determine if protease treatment would disrupt SPS protein complexes, whole blood samples from healthy donors were collected in ACD vacuum containers (BD Biosciences, Franklin Lakes, NJ). One milliliter (mL) of the whole blood was diluted 3-fold with 1.75 mL of Dulbecco's phosphate-buffered saline (DPBS, $Ca^{+2}$ and $Mg^{+2}$ free, ThermoFisher, Waltham, MA) and 0.25 mL of 1% SPS in water. A total of 8 blood samples were prepared for analysis.

Bacteria (*Escherichia coli*) were added to the blood samples at a final concentration of 90,000 colony forming units (CFU)/mL to simulate a bacteremic blood sample. The bacteremic blood samples were centrifuged briefly (500×g for three minutes) to separate the human blood cells (namely red blood cells and white blood cells) from the bacteria-enriched plasma. The pellet comprised red blood cells and white blood cells and the supernatant comprised blood plasma, bacteria, and SPS- and SPS-serum protein complexes. Two milliliters of the supernatant from the bacteremic blood samples was manually removed by pipetting and transferred to a fresh tube. This initial supernatant (S1) is treated with increasing concentrations of the protease Proteinase K (New England Biolabs, Boston, MA) (0 units (U), 4 U, 12 U, and 40 U per mL of supernatant) at 37° C. for 5 minutes, then 40 uL of 10% Triton X100 (Sigma-Aldrich, St. Louis, MO) is added to reach a final concentration of 0.2% and further incubated at 37° C. for 5 minutes. S1 is then centrifuged at 3000×g for 5 minutes and excess supernatant is removed. The original pelleted blood sample is resuspended with an additional two milliliters of 1×DPBS and then centrifuged once more at 500×g for three minutes. An additional two milliliters of the second supernatant (S2) is taken off and added to the pellet from S1 after the 3000×g spin. S2 is then treated with 40 uL of 10% Triton X100 for 5 minutes at room temperature and spun down at 3000×g. Excess supernatant is then aspirated to leave the final sample.

All experimental samples (supernatant and proteinase K) and control samples (supernatant without proteinase K) were resuspended in 900 uL of TBST (50 mM Tris-HCl, pH 7.5, 150 mM NaCl, 0.5% Tween 20 (Sigma P9416)) and further spun down at 10,000×g for 3 minutes to concentrate the bacteria and the insoluble SPS-serum protein complexes. The supernatant from this spin is completely aspirated post spin down, leaving only the pellet behind.

The pelleted samples are resuspended in 10 uL of 1×TE (10 mM Tris-HCl, pH 8.0, 0.1 mM EDTA) and lysed with 10 uL of lysis buffer (50 mM NaOH, 0.4 mM EDTA). Lysed samples are incubated at 75° C. for 10 minutes to facilitate lysis and then 10 uL of neutralization buffer (40 mM Tris-HCl, pH 8.0) is added. 15 uL of each sample was run on an agarose gel stained with SYBR-safe (Thermo Fisher, Waltham, MA) to visualize SPS contamination.

Figure 2:
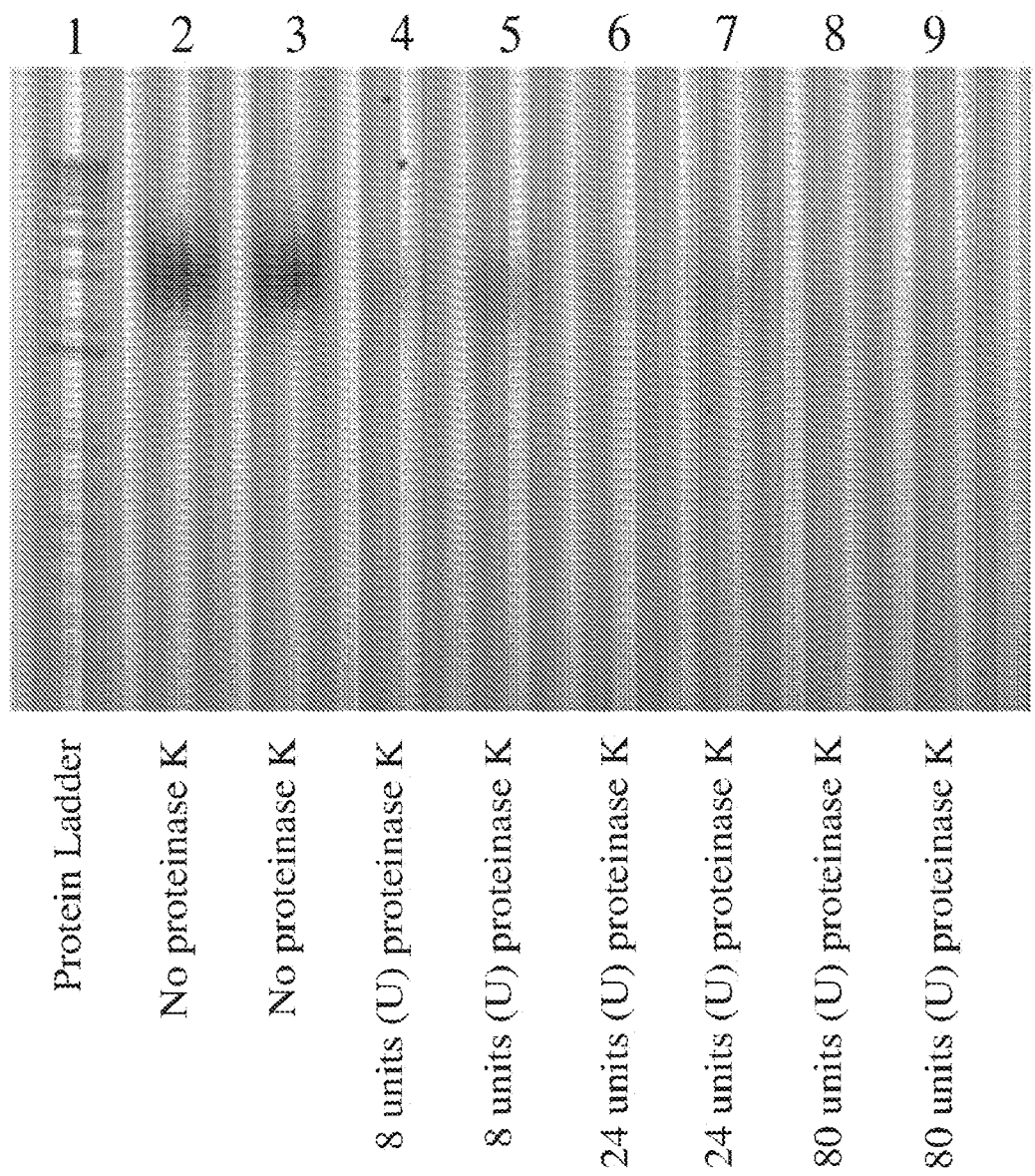
FIG. 2 demonstrates that SPS-serum protein complex formation is minimized by proteinase K treatment. Lane 1 is a 1 kb DNA ladder; lanes 2-3 are samples that were not treated with proteinase K; lanes 4-5 are samples treated with 4 units (U)/mL (8 U total) of proteinase K (New England BioLabs, Ipswich, MA); lanes 6-7 are samples treated with 12 U/mL (24 U total) of proteinase K; lanes 8-9 are samples treated with 40 U/mL (80 U total) of proteinase K.

In FIG. 2, SPS protein complex formation is minimized by proteinase K treatment. Lane 1 is a 1 kb DNA ladder, lanes 2-3 are samples that were not treated with proteinase K, lanes 4-5 are samples treated with 8 units (U) proteinase K, lanes 6-7 are samples treated with 24 U proteinase K, and lanes 8-9 are samples treated with 80 U proteinase K. The bacterial pellet from samples not comprising proteinase K were enriched for SPS and serum proteins relative to the samples comprising proteinase K (FIG. 2). Furthermore, treatment with proteinase K reduced SPS and serum proteins in the pellet in a concentration-dependent manner.

Example 3: Treatment with Proteinase K Reduces Blood Serum Proteins in Bacteremic Blood Samples Comprising SPS To determine if treatment with proteinase K results in significant soluble protein reduction, 1 mL of whole blood samples from a healthy donor were collected in vacuum liquid containers containing SPS and diluted to a final volume of 3 mL with 1×DPBS ($Ca^{+2}$ and $Mg^{+2}$ free, ThermoFisher, Waltham, MA). The samples were spiked with 10,000 CFU of *E. coli* to simulate bacteremic blood samples.

Figure 3:
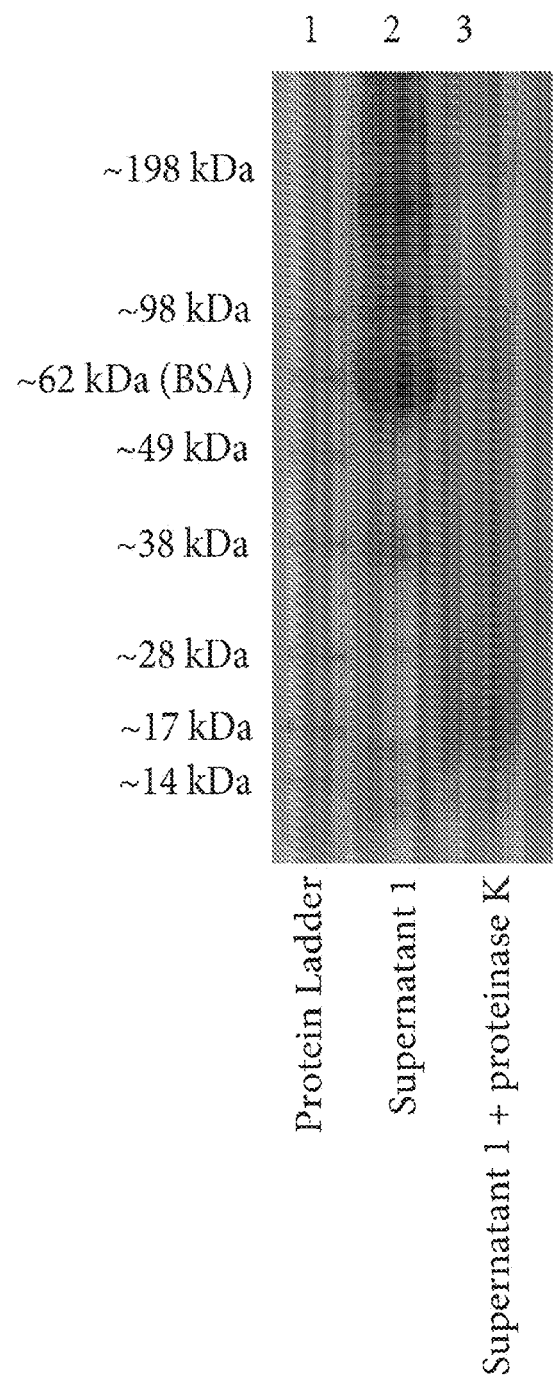
FIG. 3 illustrates that serum proteins are degraded in the supernatant after proteinase K treatment. Lane 1 is a protein ladder (SeeBlue Plus2 pre-stained protein ladder, ThermoFisher, Waltham, MA); lane 2 is proteins present in the supernatant after centrifugation of clinical blood samples diluted with DPBS; lane 3 is proteins present the supernatant after centrifugation of clinical blood samples diluted with DPBS and after proteinase K treatment for 10 minutes at 37° C.

The bacteremic blood samples were centrifuged at 500×g to pellet blood cells. The pellet contained red blood cells and white blood cells and the supernatant contained blood plasma, bacteria, and SPS-serum protein complexes. Two milliliters of the supernatant from the bacteremic blood samples was manually removed by pipetting and transferred to a fresh tube before being treated with 40 uL of 10% Triton X100 for a final concentration of 0.2% and 8 units (U) of the Proteinase K for a final concentration of 4 U/mL (FIG. 3). All samples were incubated at 37° C. for 10 minutes. Samples of the supernatant were taken before and after Proteinase K treatment, diluted with BOLT LDS sample buffer (Thermo Fisher, Waltham, MA) and loaded on a BOLT 4-12% Bis Tris Plus gel (Thermo Fisher, Waltham, MA) with MES SDS running buffer (Thermo Fisher, Waltham, MA). After the samples had been separated on the gel, the protein gel was stained with PageBlue Protein Staining Solution (Thermo Fisher, Waltham, MA) and de-stained according to manufacturer's instructions.

In FIG. 3, lane 1 is the SeeBlue-Plus2 Prestained protein standard (ThermoFisher, Waltham, MA), lane 2 is proteins present in the supernatant after centrifugation of clinical blood samples diluted with DPBS, lane 3 is proteins present in the supernatant after centrifugation of clinical blood samples diluted with DPBS after proteinase K treatment for 10 minutes at 37° C.

As seen in FIG. 3, proteinase K treatment significantly reduced soluble proteins in large clinical samples volumes and thus reduces potential SPS-protein complex formation and contamination in subsequent enriched pellets.

Example 4: Bacterial Viability is not Affected by Proteinase K Treatment

Figure 4:
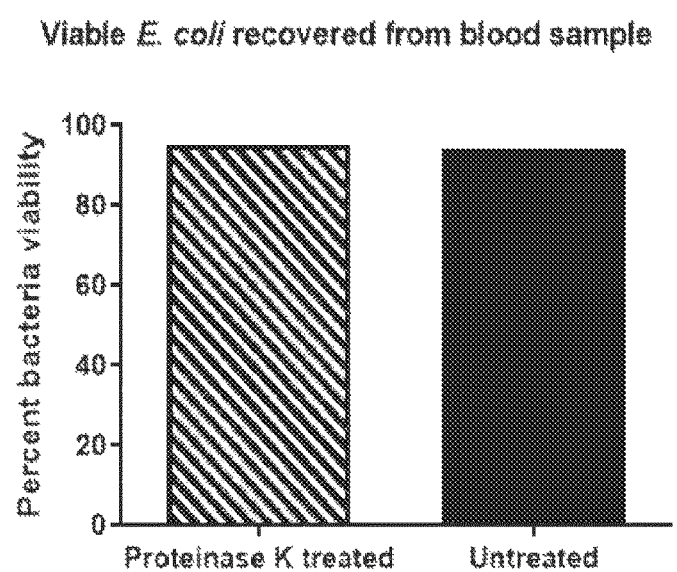
FIG. 4 illustrates the viability of *Escherichia coli* from clinical blood samples collected in SPS vacuum liquid containers that were treated with proteinase K is not decreased compared to untreated samples.

To examine the effect of proteinase K treatment on bacteria viability, clinical blood samples were collected and treated as in Example 2 with the following modifications. *Escherichia coli* (*E. coli*) bacteria were added to the diluted blood samples collected in SPS vacutainers at a final concentration of 10,000 CFU/mL. A 100 µL fraction of supernatant treated with proteinase K and a 100 µL fraction of supernatant not treated with proteinase K was cultured on agar plates. Individual colonies were counted after an overnight incubation. The viability of *E. coli* in the supernatant was not significantly inhibited by treatment with proteinase K (FIG. 4). FIG. 4 also illustrates the excellent recovery of viable bacteria from clinical blood samples collected in SPS vacuum liquid containers.

Example 5: Treatment with Proteinase K Enhances the Rate of In Vitro DNA Amplification from the Enriched Pellet of a Sample Collected with SPS Additive To examine the effect of proteinase K treatment on DNA amplification efficiency, clinical blood samples were collected in ACD vacutainers and diluted with 1×DPBS and SPS as in Example 2. Bacteria (*Escherichia coli*) were added to the blood samples at a final concentration of 1,000 CFU/mL to simulate a bacteremic blood sample. The bacteremic blood samples were centrifuged briefly at 500×g for three minutes to separate the human blood cells from the bacteria-enriched plasma. Two milliliters of the supernatant from the bacteremic blood samples was manually removed by pipetting and transferred to a fresh tube (supernatant 1, S1). The pelleted blood sample was resuspended with an additional two milliliters of 1×DPBS and then centrifuged once more at 500×g for three minutes. An additional two milliliters of this second supernatant (S2) was taken off and added to S1. The combined 4 mL of supernatant was then treated with no proteinase K or 4 U/mL of Proteinase K and a final concentration of 0.2% Triton X100 at 37° C. for 10 minutes. The samples were then spun down at 3000×g for 5 minutes to collect the bacteria. The majority of the supernatant was aspirated, leaving the concentrated sample.

All experimental samples were resuspended in 900 µL of TBST (50 mM Tris-HCl, pH 7.5, 150 mM NaCl, 0.5% Tween 20 (Sigma P9416)) and further spun down at 10,000×g for 3 minutes to concentrate the bacteria. The supernatant was completely aspirated, leaving only the pellet behind.

The concentrated, pelleted sample was then subjected to the REPLI-g Single Cell MDA protocol with supplementation of the MDA reaction buffer with 0.5% BSA (Sigma-Aldrich, St. Louis, MO). Time-point samples were taken after 1.5, 2.5, and 4 hours of incubation/MDA at 30° C. To quantify the bacterial DNA concentration, 16S rRNA gene concentrations were measured with a custom 16S rRNA TaqMan probe and the TaqMan Fast Advanced Master Mix. Total amplified DNA was quantified using the Qubit dsDNA HS Assay kit (ThermoFisher, Waltham, MA).

Figure 5A:
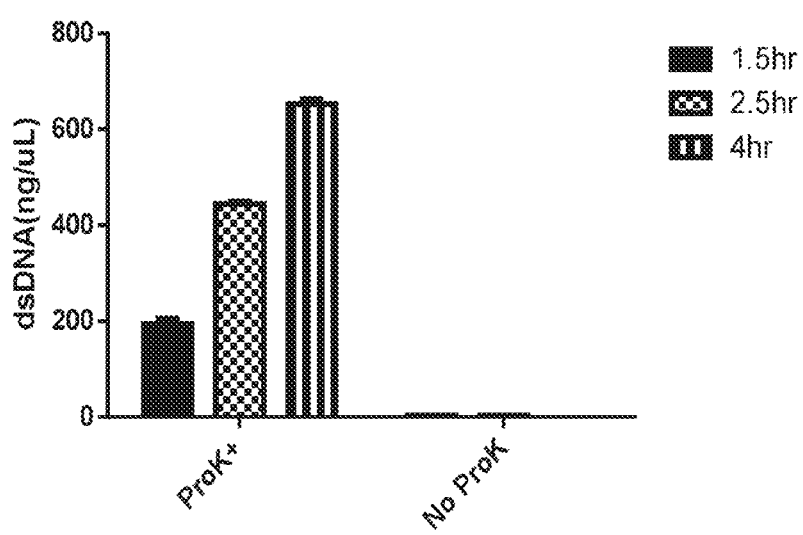
FIGS. 5A-5B illustrate that the addition of proteinase K treatment to SPS-containing clinical samples results in a significant improvement in total (FIG. 5A) and bacterial-specific (FIG. 5B) DNA yield after DNA amplification after 1.5, 2.5, and 4 hours of amplification time.
Figure 5B:
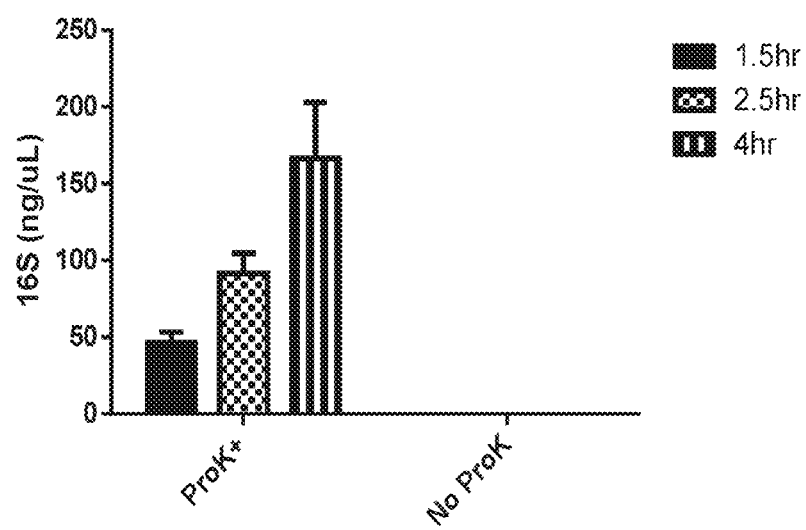

FIG. 5A illustrates that the addition of proteinase K enhances the rate of total DNA amplification by at least 100-fold when compared to samples not treated with proteinase K at the 1.5, 2.5, and 4 hour time points. FIG. 5B illustrates that, similar to total DNA amplification, bacteria DNA amplification, as measured by 16S signal, is also increased by at least 100-fold when compared to samples not treated with proteinase K.

Figure 6:
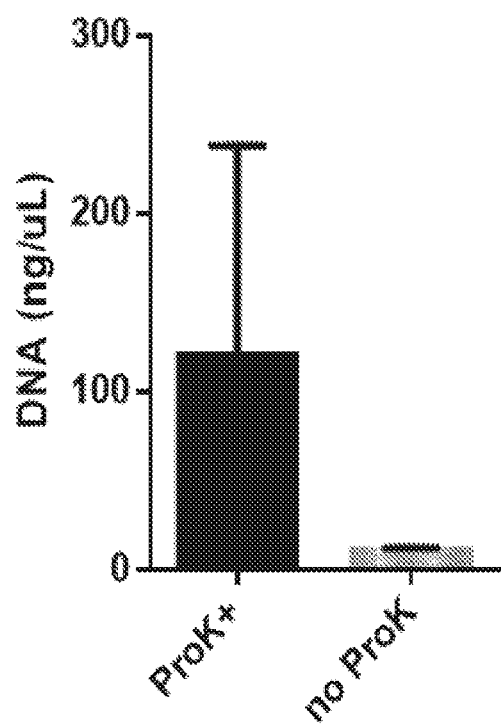
FIG. 6 illustrates that the addition of proteinase K treatment to sample preparation from blood collected in lithium heparin vacutainers results in an improvement in DNA yield after DNA amplification.

Example 6: Treatment with Proteinase K Enhances the Rate of In Vitro DNA Amplification from Samples Collected in Lithium Heparin Vacuum Liquid Containers Blood from healthy donors was collected into lithium heparin vacutainers (Becton Dickinson, Franklin Lakes, NJ). Replicates of 4 mL of blood were spiked with 2.5 CFU/mL of *E. coli* and diluted with 8 mL of 1×DPBS. Bacteria-enriched plasma supernatant was produced by two serial centrifugations at 500×g as described in Example 2. Half of the supernatants were treated with Proteinase K (final concentration 4 U/mL) and all supernatants were treated with 10% Triton X-100 (final concentration of 0.2%) followed by a 10 minute incubation at 37° C. All supernatant samples were then pelleted with a high-speed centrifugation at 3,000×g for 10 minutes. The pellets were resuspended in 1×DNase I buffer and treated with DNase I (final concentration of 40 U/mL; New England Biolabs, Boston, MA) for 15 minutes at 37° C. The DNase-treated samples were then pelleted at 10,000×g for 3 minutes, washed in 1 mL TBST, and pelleted again. The supernatant was aspirated, and the DNA contained with the pellets was amplified using the REPLI-g Single Cell MDA protocol. As shown in FIG. 6, the addition of proteinase K enhanced by the amplification of bacterial DNA by an average of 10 fold relative to control samples that were not treated with proteinase K (FIG. 6).

Example 7: Synthesis of RNA Libraries from Microbes Isolated from Bacteremic Patients Similar to DNA polymerases, reverse transcriptase function is inhibited by polyanionic polymers (e.g., SPS, heparin) (Kiehl, et al., 1973, Anticoagulants as Inhibitors of Reverse Transcriptase Activity, Journal of the National Cancer Institute, 51(5): 1705-1707). Thus, the absence of polymerase inhibitors is crucial for the preparation of complementary DNA (cDNA) libraries and subsequent transcriptomes from clinical samples. The use of proteinase K treatment to mitigate polyanionic polymer (e.g., SPS, heparin) inhibitory effects can also be used to enable the determination of transcriptional profiles of microbial or human cells from bacteremic patients. This could be used clinically to predict antibiotic resistance, for example (Khaledi, et al., 2016, Transcriptome Profiling of Antimicrobial Resistance in *Pseudomonas aeruginosa*, Antimicrobial Agents and Chemotherapy, 60(8): 4722-4733).

A cDNA library will be prepared from a clinical sample utilizing any of the numerous protocols in the art. For example, the clinical sample will be treated with proteinase K as described in the claims and the desired microbial DNA will be isolated through centrifugation. The total RNA in the sample will be extracted using the PicoPure RNA isolation kit (ThermoFisher, Waltham, MA) with random hexamers or any other appropriate primers.

What is claimed is:

1. A method for preparing a clinical sample from a subject comprising microbes, cells of the subject, and at least one polyanionic polymer nucleic acid amplification inhibitor that binds at least one protein in the sample, comprising the steps of:

(a) obtaining the clinical sample from the subject comprising the microbes, the at least one protein, and the at least one polyanionic polymer nucleic acid amplification inhibitor;
(b) separating the clinical sample into:
  (i) a first fraction comprising the cells of the subject, and
  (ii) a second fraction comprising the microbes and the at least one polyanionic polymer nucleic acid amplification inhibitor bound to the at least one protein;
(c) adding to the second fraction a protease which degrades the at least one protein; and
(d) separating the second fraction into:
  (i) a third fraction comprising the microbes and any remaining cells from the subject, and
  (ii) a fourth fraction comprising the at least one polyanionic polymer nucleic acid amplification inhibitor;
wherein the microbe is a pathogenic microbe, wherein the pathogenic microbe is *Staphylococcus aureus* (*S. aureus*), *Staphylococcus epidermidis* (*S. epidermidis*), *Streptococcus agalactiae* (*S. agalactiae*), *Enterococcus faecalis* (*E. faecalis*), *Enterococcus faecium* (*E. faecium*), *Escherichia coli* (*E. coli*), or *Klebsiella pneumoniae* (*K. pneumoniae*).

2. The method of claim 1, wherein the separating is by centrifugation.

3. The method of claim 1, wherein the separating is by filtration.

4. The method of claim 1, wherein the separating is by microfluidic size exclusion.

5. The method of claim 1, wherein the separating is by plasma tubes.

6. The method of claim 1, wherein the separating is by immunoprecipitation.

7. The method of claim 1, wherein the clinical sample is blood, sputum, urine, mucus, saliva tissue abscess, wound drainage, lymph, lavage, stool, cerebral spinal fluid, or any fluid aspirate or tissue extraction of human or other mammalian origin.

8. The method of claim 1, wherein the at least one polyanionic polymer nucleic acid amplification inhibitor is sodium polyanethol sulfonate or heparin.

9. The method of claim 1, wherein the obtaining step utilizes a vacuum liquid container or blood culture bottle.

10. The method of claim 1, wherein the protease is proteinase K, Factor Xa, Arg-C proteinase, Asp-N endopeptidase, Asp-N endopeptidase+N-terminal Glu, 3-Bromo-3-methyl-2-(2-nitropheylthio)-3H-indole (BNPS-Skatole), Caspase1, Chymotrypsin-high specificity, Clostripain, cyanogen bromide (CNBr), Enterokinase, Granzyme B, formic acid, glutamyl endopeptidase, hydroxylamine, iodosobenzoic acid, LysC, LysN, 2-nitro-5-thiocyanatobenzoic acid (NTCB), pepsin, proline-endopeptidase, staphylococcal peptidase I, tobacco etch virus protease, thermolysin, thrombin, or trypsin.

11. The method of claim 1, wherein the amount of protease added is between 5 units/mL (U/mL) and 5000 units/mL (U/mL).

12. The method of claim 1, wherein the protease and the second fraction are incubated at between 20° C. and 55° C. for at least 10 minutes.

13. The method of claim 1, further comprising the step of nucleic acid amplification of nucleic acids in the third fraction.

14. The method of claim 13, wherein the nucleic acid amplification is isothermal strand-displacement amplification, polymerase chain reaction (PCR), quantitative PCR (qPCR), reverse transcriptase PCR (RT-PCR), degenerate oligonucleotide PCR, or primer extension pre-amplification.

15. The method of claim 13, wherein addition of the protease increases the amplification of microbial nucleic acid by at least 5-fold relative to samples in which protease has not been added.

16. The method of claim 1, further comprising a step of removing the second fraction from the first fraction after step (b).

17. The method of claim 16, wherein the protease which degrades the at least one protein of step (c) is added before or after the second fraction is removed from the first fraction.

18. A method for preparing a clinical sample from a subject comprising microbes, cells of the subject, and at least one polyanionic polymer nucleic acid amplification inhibitor that binds at least one protein in the sample, comprising the steps of:
(a) obtaining the clinical sample from the subject comprising the microbes, the at least one protein and the at least one polyanionic polymer nucleic acid amplification inhibitor;
(b) adding to the clinical sample a protease which degrades the at least one protein;
(c) separating the clinical sample into:
  (i) a first fraction comprising the cells of the subject, and
  (ii) a second fraction comprising the microbes and the at least one polyanionic polymer nucleic acid amplification inhibitor bound to the at least one protein;
(d) removing the second fraction from the first fraction; and
(e) separating the second fraction into:
  (i) a third fraction comprising the microbes, and
  (ii) a fourth fraction comprising the at least one polyanionic polymer nucleic acid amplification inhibitor.

19. A method for preparing a clinical sample from a subject comprising microbes, cells of the subject, and at least one polyanionic polymer nucleic acid amplification inhibitor that binds at least one protein in the sample, comprising the steps of:
(a) obtaining the clinical sample from the subject comprising the microbes, the at least one protein, and the at least one polyanionic polymer nucleic acid amplification inhibitor;
(b) selectively lysing the microbes;
(c) adding to the clinical sample a protease which degrades the at least one protein; and
(d) separating the clinical sample into:
  (i) a first fraction comprising the cells of the subject, and
  (ii) a second fraction comprising nucleic acid from the microbes.

* * * * *